(12) United States Patent
Wang et al.

(10) Patent No.: US 11,884,639 B2
(45) Date of Patent: Jan. 30, 2024

(54) PREPARATION METHOD FOR HIGH OPTICAL INDOXACARB INTERMEDIATE

(71) Applicant: SHANDONG JINGBO AGROCHEMICALS TECHNOLOGY CO., LTD., Shandong (CN)

(72) Inventors: Zhongyang Wang, Binzhou (CN); Daoquan Cheng, Binzhou (CN); Tingchao Pang, Binzhou (CN); Ping Wang, Binzhou (CN); Jiancheng Liu, Binzhou (CN); Renping Han, Binzhou (CN); Lianyou Yu, Binzhou (CN); Nengchun Wei, Binzhou (CN)

(73) Assignee: SHANDONG JINGBO AGROCHEMICALS TECHNOLOGY CO., LTD., Binzhou (CN)

( * ) Notice: Subject to any disclaimer, the term of this patent is extended or adjusted under 35 U.S.C. 154(b) by 888 days.

(21) Appl. No.: 16/772,435

(22) PCT Filed: Apr. 25, 2019

(86) PCT No.: PCT/CN2019/084264
§ 371 (c)(1),
(2) Date: Jun. 12, 2020

(87) PCT Pub. No.: WO2019/233211
PCT Pub. Date: Dec. 12, 2019

(65) Prior Publication Data
US 2021/0363118 A1 Nov. 25, 2021

(30) Foreign Application Priority Data
Jun. 8, 2018 (CN) .......................... 201810589157.0

(51) Int. Cl.
| | | |
|---|---|---|
| *C07D 273/04* | (2006.01) | |
| *B01J 31/16* | (2006.01) | |
| *B01J 31/22* | (2006.01) | |
| *C07B 53/00* | (2006.01) | |
| *C07C 67/31* | (2006.01) | |

(52) U.S. Cl.
CPC ........ *C07D 273/04* (2013.01); *B01J 31/1658* (2013.01); *B01J 31/2217* (2013.01); *C07B 53/00* (2013.01); *C07C 67/31* (2013.01); *B01J 2231/70* (2013.01); *B01J 2531/0252* (2013.01); *B01J 2531/48* (2013.01); *C07B 2200/07* (2013.01); *C07C 2602/08* (2017.05)

(58) Field of Classification Search
CPC . C07D 273/04; B01J 31/1658; B01J 31/2217; B01J 2231/70; B01J 2531/0252; B01J 2531/48; B01J 31/2243; C07B 53/00; C07B 2200/07; C07C 67/31; C07C 2602/08; C08F 8/42; C08F 112/34; Y02P 20/584
USPC .......................................................... 544/66
See application file for complete search history.

(56) References Cited

FOREIGN PATENT DOCUMENTS

| | | |
|---|---|---|
| CN | 1630555 A | 6/2005 |
| CN | 105521826 A | 4/2016 |
| WO | 03/040083 A1 | 5/2003 |

OTHER PUBLICATIONS

Yang et al., "Enantioselective α-Hydroxylation by Modified Salen-Zirconium(IV)-Catalyzed Oxidation of β-Keto Esters," Organic Letters, vol. 19, No. 33, Jan. 12, 2017, pp. 448-451.
Zhifeng Dai et al., "Enhancement of Catalytic Activity in Epoxide Hyrdation by Increasing the Concentration of Cobalt (III)/Salen in Porous Polymer Catalysts," ChemCatChem Full Papers, vol. 8, 2016, pp. 812-817.
Jun. 27, 2019 International Search Report issued in International Patent Application No. PCT/CN2019/084264.

*Primary Examiner* — Taylor V Oh
(74) *Attorney, Agent, or Firm* — Oliff PLC

(57) ABSTRACT

A field of asymmetric catalytic synthesis, and in particular a preparation method for a high optical indoxacarb intermediate includes reacting 5-chloro-2-methoxycarbonyl-1-indanone ester (or indanone ester for short) with an oxidizing agent in the presence of a chiral Zr-salen polymer to obtain an indoxacarb intermediate (2S)-5-chloro-2,3-dihydro-2-hydroxy-1-oxo-1H-indole-2-carboxylic acid methyl ester. The yield is stabilized between 86% and 90%, and the S-enantiomer content is up to 99%. Such catalyst can replace catalysts such as cinchonine, and greatly increase the content of the effective S-enantiomer of the indoxacarb, so that the content of the hydroxyl intermediate S-enantiomer of the indoxacarb is raised from 75% to 99% or more. In addition, the chiral Zr-salen polymer catalyst is recycled without retreatment, and can be recycled at least 5 times or more, greatly reducing the production cost and laying a foundation for the industrial production of high quality indoxacarb.

10 Claims, No Drawings

PREPARATION METHOD FOR HIGH OPTICAL INDOXACARB INTERMEDIATE

Technical Field

The invention relates to the field of asymmetric catalytic synthesis, and particularly relates to a preparation method of a high optical indoxacarb intermediate, in particular to a method for preparing a high optical indoxacarb intermediate (2S)-5-chloro-2,3-dihydro-2-hydroxy-1-oxo-1H-indene-2-carboxylic acid methyl ester by using a high-efficiency Zr-salen polymer as a catalyst.

Background Technology

Indoxacarb is a new, highly effective and low toxic oxadiazine pesticide developed by DuPont Company of the United States. It has double effects of contact killing and stomach toxicity, and effectively solves resistant pests. Indoxacarb, due to its unique mechanism of action and broad market prospects, is a substitute for high toxicity and high residue pesticide varieties widely demonstrated and popularized by China's Ministry of Agriculture.

With the end of indoxacarb patent period, many domestic enterprises began to research the synthesis process of products and produce them, but the original pesticide of indoxacarb that they achieved through synthesis is a mixture of S and R (S:R=3:1), in which the R-enantiomer in the original pesticide has no efficacy but causes environmental pollution and high cost of medicine. Therefore, the development of a synthetic method of the S-indoxacarb has become a hot topic at home and abroad. At present, there are three main catalysts used in the synthesis of indoxacarb:

First, using quinine catalysts such as cinchonine, but the efficiency of these catalysts is low, and the content of the hydroxyl intermediate S-enantiomer of the indoxacarb is about 75%.

Second, using metal complex catalysts. In 2005, DuPont Company reported a zirconium catalyst in publication CN1630555A, which can increase the content of the S-enantiomer of the indoxacarb to 99%, but the usage of the catalyst is large, more than 15% of the weight of indanone ester. The catalyst mentioned in the publication is homogeneous in the system, which is not easy to recycle, and can be utilized only after reprocessing. Moreover, the catalytic effect of this kind of catalyst can be significantly reduced when it is recycled once without adding new catalyst. And times of recycling are limited, and the production cost is high.

Third, biological enzyme method using the selected special enzyme can increase the content of the S-enantiomer of the indoxacarb to 99%, but the production cost of this method is very high and the production efficiency is low, so it is not suitable for large-scale industrial production.

The optical level of indoxacarb intermediate (2S)-5-chloro-2,3-dihydro-2-hydroxy-1-oxo-1H-indene-2-carboxylic acid methyl ester directly determines the final optical level of indoxacarb, so how to overcome the defects of catalyst and synthesis method in the synthesis process of indoxacarb intermediate becomes one of the problems to be solved in the field.

Content of Invention

Aiming at the defects of the prior art, this invention provides a method for preparing a high optical indoxacarb intermediate (2S)-5-chloro-2,3-dihydro-2-hydroxy-1-oxo-1H-indene-2-carboxylic acid methyl ester, which is suitable for industrialized production. This invention adopts a brand-new catalyst, which the catalyst can be used for preparing indoxacarb instead of the original catalysts such as cinchonine and the like. The high molecular effect enables the reaction effect of the heterogeneous catalytic reaction system to reach the reaction effect of the homogeneous catalytic system; the catalyst is convenient to recycle, which can be recycled for more than 5 times on the basis of not supplementing the new catalyst; the content of the hydroxyl intermediate S-enantiomer of the indoxacarb is kept above 99%; and according to the optical requirements of products, the catalyst dosage or recycling times can be adjusted to meet the requirements for preparing indoxacarb with different optical contents. Thus the production cost of high-optical indoxacarb is greatly reduced, which lays a solid foundation for its industrialized production.

The technical scheme of the invention is as follows:

The inventor first provided a brand-new chiral catalyst containing zirconium, namely chiral Zr-salen polymer, and the preparation reaction equation is as follows:

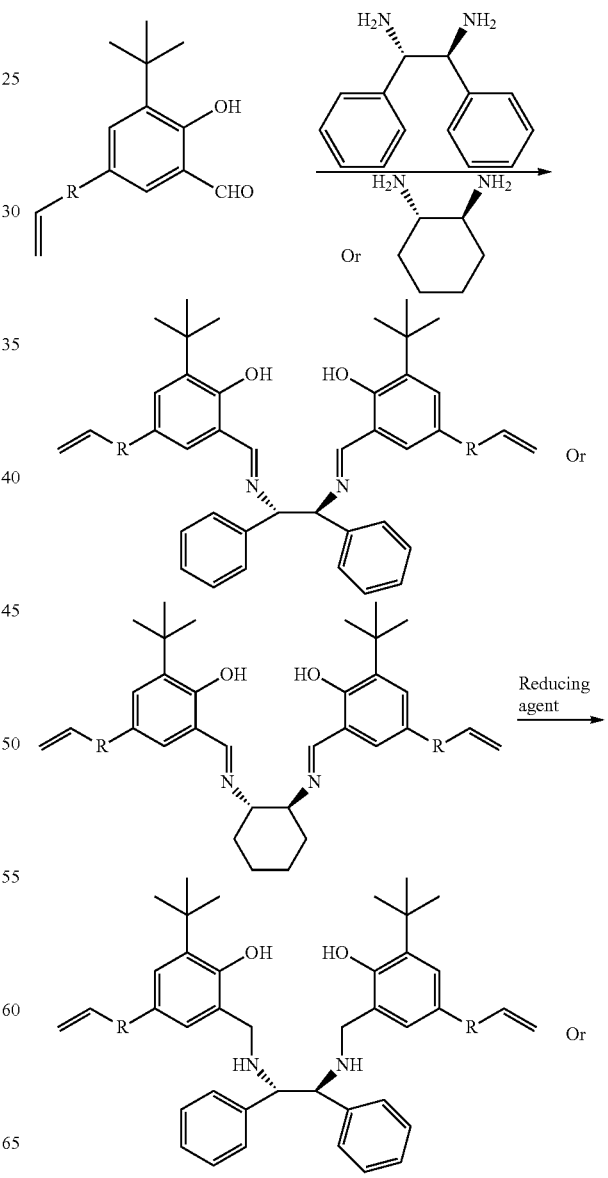

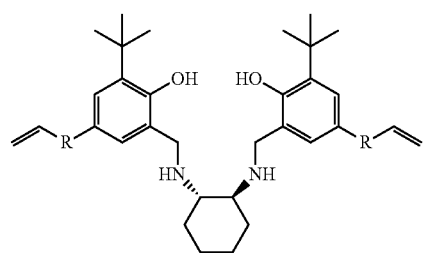

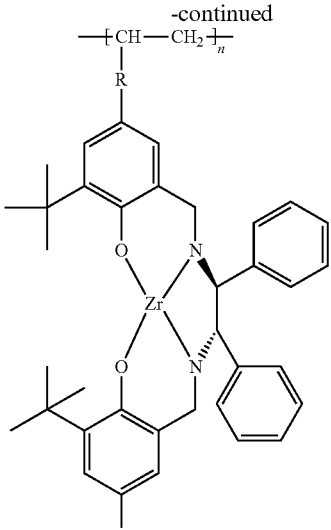

Catalyst A

Or

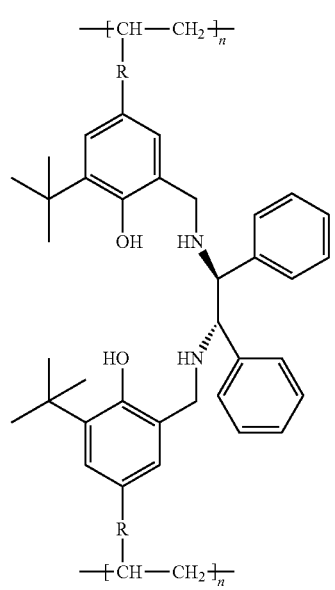

Or

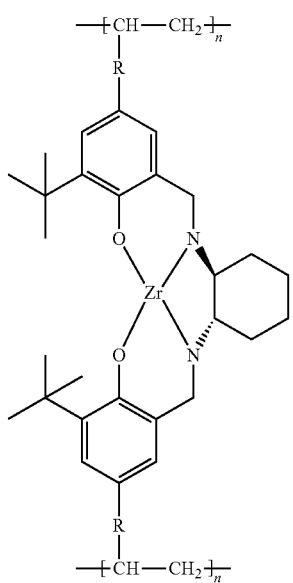

Catalyst B

Wherein: R is

 or ——, n is 100~20000.

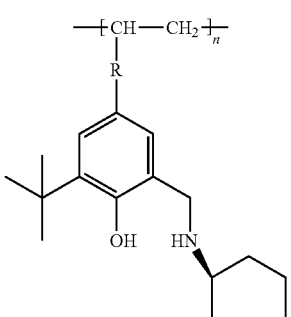

The specific steps are as follows:

(1) Adding solvent I, 3-tert-butyl-5-styrylsalicylaldehyde and (1S,2S)-(−)-1,2-diphenylethylenediamine or (1S,2S)-(+)-1,2-cyclohexanediamine into a reaction flask. Raising the temperature for reflux reaction. After the reaction is finished, and a condensate is obtained after lowering the temperature and filtration.

(2) Dissolving the condensate in solvent II. Raising the temperature to 50-60° C., and dripping a reducing agent.

Removing the solvent II after the reaction. Adding water into the system, and a ligand monomer of catalyst A or catalyst B is obtained after extraction, desolation, crystallization, lowering the temperature and filtration.

(3) Putting the ligand monomer of catalyst A or catalyst B into a pressure-resistant reaction flask. Using ethanol/water as a solvent III and azobisisobutyronitrile (AIBN) as an initiator, carrying out hydrothermal polymerization at 110-120° C. A polymer ligand is obtained after filtration and drying.

(4) Putting the polymer ligand and zirconium-containing metal compound in toluene at 50-80° C. to carry out complexation reaction. After the reaction, a toluene system of catalyst A or catalyst B is obtained.

In the above preparation process:

In step (1), the solvent I is methanol. Duration of the reflux reaction is 6-7 h. The mole ratio of 3-tert-butyl-5-styrylsalicylaldehyde and (1S,2S)-(−)-1,2-diphenylethylenediamine or (1S,2S)-(+)-1,2-cyclohexanediamine is 2:1-1.1. The dosage of the solvent I is 8-10 times of the mass of (1S,2S)-(−)-1,2-diphenylethylenediamine or (1S,2S)-(+)-1,2-cyclohexanediamine.

The 3-tert-butyl-5-styrylsalicylaldehyde used in step (1) is prepared by bromination of 3-tert-butylsalicylaldehyde and then coupling reaction with 4-vinylphenylboronic acid. The raw material is easy to obtain. The specific reaction process can refer to reference: preparation of dendritic and non-Dendritic styryl-Substituted salens for cross-Linking suspension copolymerization with styrene and multiple use of the corresponding Mn and Cr complexes in enantioselective epoxidations and Hetero-Diels-Alder reactions.

In step (2), the solvent II is tetrahydrofuran. The reducing agent is sodium borohydride or sodium cyanoborohydride or potassium borohydride or lithium aluminum hydride. The mole ratio of the reducing agent and the condensate is 2-4:1; the dosage of the solvent TT is 4-8 times of the mass of the condensate. The reducing agent is usually dissolved in solvent II alone for dripping. Carrying out heat preservation reaction for 0.5 h after drop adding.

The weight of the water added in step (2) is 2-4 times of the weight of the condensate. Extraction with ethyl acetate, and the weight of ethyl acetate added is 6-10 times of the weight of the condensate. The crystallization solvent is methanol. The dosage of methanol is 4-8 times of the weight of the condensate.

In step (3), the solvent III is the mixture of ethanol and water. The volume ratio of ethanol to water is 3:1. The dosage of the solvent III is 6-10 times of the weight of the ligand monomer of Catalyst A or Catalyst B, and the dosage of AIBN is 0.5%~2% of the weight of the ligand monomer of Catalyst A or Catalyst B. The reaction duration is 16-20 h, and the reaction pressure is 0.3 to 0.5 MPa. Among them, the volume ratio of ethanol to water and the dosage of the solvent III have a greater impact on the particle size of the polymer in the later stage. Different ratios will get polymers with different sizes. Using the conditions described in this Invention, the particle size of the polymer can be controlled within 0.1 to 1 mm.

In step (3), the particle size of the polymer ligand is 0.1-1 mm. If the catalyst particle size is too small, the loss of the catalyst in the reaction process is large, and the catalyst is hard to be recycled; if the catalyst particle size is too large, the contact area between catalyst and reaction substrate is small, resulting in a long reaction period, which will affect the catalytic effect of catalyst.

The zirconium compound in step(4) is selected from zirconium hydroxide, zirconyl chloride octahydrate, zirconium dioxide, zirconium(IV) acetylacetonate, zirconium trifluoroacetylacetonate, n-propyl zirconate, zirconium(IV) tert-butoxide, zirconium(IV) hydrogenphosphate and zirconium(IV) bromide, and mixtures thereof.

In step (4), the mole ratio of the polymer ligand to the zirconium-containing metal compound is 1-1.5:1. The dosage of the toluene is 4-10 times of the weight of the polymer ligand.

Adding 5-chloro-2-methoxycarbonyl-1-indanone ester in toluene solution into the toluene system of catalyst A or catalyst B obtained by the above method, dripping oxidant at 50-80° C. to carry out asymmetric synthesis reaction. After the reaction is finished, cooling it to 60-65° C. Catalyst A or Catalyst B is recovered by hot filtration. After the filtrate is concentrated, cooled and filtered, the high optical indoxacarb intermediate (2S)-5-chloro-2,3-dihydro-2-hydroxy-1-oxo-1H-indene-2-carboxylic acid methyl ester is obtained; at the same time, the recovered Catalyst A or Catalyst B is put into toluene solvent to form a suspension, which can continue to participate in the above asymmetric synthesis reaction. The specific reaction route is as follows:

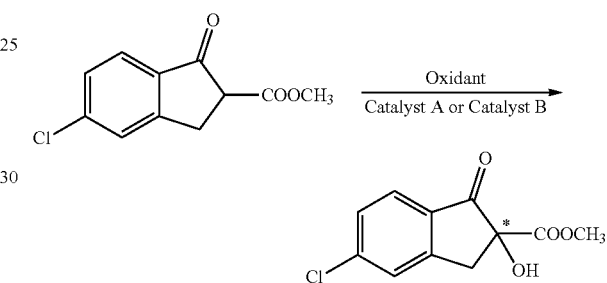

Wherein the oxidant is tert-butyl hydroperoxide or m-chloroperbenzoic acid or cumyl hydroperoxide; in terms of the mole ratio of pure matter, the oxidant to 5-chloro-2-methoxycarbonyl-1-indanone ester is 1:1.2-3; the added dosage of catalyst A or catalyst B is 1%-5% of the mass of 5-chloro-2-methoxycarbonyl-1-indanone ester; in the 5-chloro-2-methoxycarbonyl-1-indanone ester in toluene solution, the dosage of toluene is 2-4 times of the weight of 5-chloro-2-methoxycarbonyl-1-indanone ester.

The present invention adopts a high-efficiency Zr-salen polymer catalyst, which is an asymmetric catalytic oxidation catalyst. Electron and stereo effects of catalyst substituents induce oxidation reaction with high enantioselectivity to proceed, which improves the reaction selectivity. The content of the hydroxyl intermediate S-enantiomer of the indoxacarb is raised from 75% to more than 99%. The introduction of the organic polymerization ligand realizes the recycling of the high-efficiency chiral catalyst, greatly reduces the production cost. Synthesis process of this catalyst is simple, which is favorable for industrialization, and lays a good foundation for the production of high-quality indoxacarb.

Specific Embodiments

Embodiment 1 (Taking Catalyst A as an Example)

A preparation method for high optical indoxacarb intermediate, the preparation method is as follows:

1. Adding 28 g (0.1 mol) of 3-tert-butyl-5-styrylsalicylaldehyde and 10.6 g (0.05 mol) of (1S,2S)-(−)-1,2-diphenylethylenediamine to a reaction flask, then adding 106 g of methanol to the reaction flask and the mixture is heated and refluxed. Cooling the mixture to 0~5° C. and a pale yellow condensate solid is obtained after filtration. The weight of the condensate solid is weighed as 35 g after drying, and the yield is 95%.

2. Weighing and dissolving 7.36 g (0.01 mol) of the above dried condensate in 50 g of tetrahydrofuran, raising the temperature to 50~60° C., add 1.5 g (0.04 mol) of sodium borohydride in batches. After the reaction, removing the tetrahydrofuran. Adding 20 g of water into the system, extracting with 60 g of ethyl acetate. After removing ethyl acetate, adding 20 g of methanol to crystallize. Lowering the temperature to 0~5° C. and filtering to obtain 6.66 g of ligand monomer of Catalyst A, with a yield of 90%. The ligand monomer is white solid and its melting point is 165-168° C., $^1$HNMR (DMSO-d6, D2O 400 MHz): δ (ppm) 1.39 (s, 18H), 3.57-3.61 (d, J=14.1 Hz, 2H), 3.68-3.72 (d, J=13.8 Hz, 2H), 3.97 (s, 2H), 5.22-5.25 (d, J=11.4 Hz, 2H), 5.79-5.83 (d, J=17.7 Hz, 2H), 6.69-6.76 (m, 2H), 6.97-6.98 (d, J=1.68 Hz, 2H), 7.14-7.23 (m, 10H), 7.32-7.33 (d, J=1.92 Hz, 2H), 7.47 (s, 8H).

3. Adding 6 g (8 mmol) of Catalyst A ligand monomer into a pressure resistant reaction flask. Adding 60 g of ethanol/water and 0.06 g of AIBN. Hydrothermal polymerization is carried out at 115-120° C. for 24 h to obtain a white-like spherical polymer ligand. The polymerization degree is 900-1500, the particle size is 0.5 mm, and the dry weight is 6 g. The yield is calculated as 100%.

4. Adding 3 g (4 mmol) of the polymer ligand and 2 g (4 mmol) of zirconium(IV) acetylacetonate to 20 g of toluene. After complexation reaction at 75~80° C. for 24 h, a catalyst A toluene suspension system was obtained. The yield of the Catalyst A is calculated as 100% and its weight is 3.3 g.

5. Dissolving 66 g (0.29 mol) of indanone ester in 132 g of toluene, and then putting the mixture into the above-mentioned 3.3 g (4 mmol) of Catalyst A toluene suspension system. Dripping into the system 45.7 g (0.41 mol) of aqueous solution of tert-butyl hydroperoxide with mass fraction 80%. Dripping time is 2 h and the reaction temperature is 75-80° C.

6. After the oxidant is dripped, maintaining the temperature at 75-80° C. for 1 h. Taking the sample to inspect the reaction.

7. After tracking reaction and confirming the reaction is qualified, cooling down to 60~65° C., and Catalyst A is recovered by hot filtration.

8. Concentrating the filtrate and toluene which the weight is 70% of the weight of the added solvent is concentrated from the filtrate. Cooling it to 0~5° C., and maintaining the temperature for 1 h. 60.6 g (converted to 100% purity calculation, the same below) of white solid (2S)-5-chloro-2,3-dihydro-2-hydroxy-1-oxo-1H-indene-2-carboxylic acid methyl ester is obtained after filtration. The optical detection of a chiral chromatographic column is 99.9%, and the yield is 86.9%.

Embodiment 2 (Taking Catalyst A as an Example)

1. The polymer ligand is prepared first, which is the same as in Embodiment 1.

2. Adding 3 g (4 mmol) of the polymer ligand and 1.55 g (4 mmol) of zirconium(IV) tert-butoxide to 20 g of toluene. After complexation reaction at 75~80° C. for 20 h, a catalyst A toluene suspension system was obtained. The yield of the Catalyst A is calculated as 100% and its weight is 3.3 g.

3. Dissolving 66 g (0.29 mol) of indanone ester in 132 g of toluene, and then putting the mixture into the above-mentioned 3.3 g (4 mmol) of Catalyst A toluene suspension system. Dripping into the system 45.7 g (0.41 mol) of aqueous solution of tert-butyl hydroperoxide with mass fraction 80%. Dripping time is 2.5 h and the reaction temperature is 75-80° C.

4. After the oxidant is dripped, maintaining the temperature at 75-80° C. for 1 h. Taking the sample to inspect the reaction.

5. After tracking reaction and confirming the reaction is qualified, cooling down to 60~65° C., and Catalyst A is recovered by hot filtration.

6. Concentrating the filtrate and toluene which the weight is 70% of the weight of the added solvent is concentrated from the filtrate. Cooling it to 0~5° C., and maintaining the temperature for 1 h. 60.96 g of white solid (2S)-5-chloro-2,3-dihydro-2-hydroxy-1-oxo-1H-indene-2-carboxylic acid methyl ester is obtained after filtration. The optical detection of a chiral chromatographic column is 99.5%, and the yield is 87.4%.

The first time for reusing the Catalyst A:

1. Dissolving 66 g (0.29 mol) of indanone ester in 132 g of toluene, and then putting the above recovered Catalyst A into the system. Dripping into the system 45.7 g (0.41 mol) of aqueous solution of tert-butyl hydroperoxide with mass fraction 80%. Dripping time is 3 h and the reaction temperature is 75-80° C.

2. After the oxidant is dripped, maintaining the temperature at 75-80° C. for 1 h. Taking the sample to inspect the reaction.

3. After tracking reaction and confirming the reaction is qualified, cooling down to 60~65° C., and Catalyst A is recovered by hot filtration.

4. Concentrating the filtrate and toluene which the weight is 70% of the weight of the added solvent is concentrated from the filtrate. Cooling it to 0~5° C., and maintaining the temperature for 1 h. 62.56 g of white solid (2S)-5-chloro-2,3-dihydro-2-hydroxy-1-oxo-1H-indene-2-carboxylic acid methyl ester is obtained after filtration. The optical detection of a chiral chromatographic column is 99.5%, and the yield is 89.7%.

The second time for reusing the Catalyst A:

1. Dissolving 66 g (0.29 mol) of indanone ester in 132 g of toluene, and then putting the above recovered Catalyst A into the system. Dripping into the system 45.7 g (0.41 mol) of aqueous solution of tert-butyl hydroperoxide with mass fraction 80%. Dripping time is 2 h and the reaction temperature is 75-80° C.

2. After the oxidant is dripped, maintaining the temperature at 75-80° C. for 1 h. Taking the sample to inspect the reaction.

3. After tracking reaction and confirming the reaction is qualified, cooling down to 60~65° C., and Catalyst A is recovered by hot filtration.

4. Concentrating the filtrate and toluene which the weight is 70% of the weight of the added solvent is concentrated from the filtrate. Cooling it to 0~5° C., and maintaining the temperature for 1 h. 61.2 g of white solid (2S)-5-chloro-2,3-dihydro-2-hydroxy-1-oxo-1H-indene-2-carboxylic acid methyl ester is obtained after filtration. The optical detection of a chiral chromatographic column is 99.8%, and the yield is 87.7%.

The third time for reusing the Catalyst A:

1. Dissolving 66 g (0.29 mol) of indanone ester in 132 g of toluene, and then putting the above recovered Catalyst A into the system. Dripping into the system 45.7 g (0.41 mol)

of aqueous solution of tert-butyl hydroperoxide with mass fraction 80%. Dripping time is 2.5 h and the reaction temperature is 75-80° C.

2. After the oxidant is dripped, maintaining the temperature at 75-80° C. for 1 h. Taking the sample to inspect the reaction.

3. After tracking reaction and confirming the reaction is qualified, cooling down to 60~65° C., and Catalyst A is recovered by hot filtration.

4. Concentrating the filtrate and toluene which the weight is 70% of the weight of the added solvent is concentrated from the filtrate. Cooling it to 0~5° C., and maintaining the temperature for 1 h. 62.0 g of white solid (2S)-5-chloro-2,3-dihydro-2-hydroxy-1-oxo-1H-indene-2-carboxylic acid methyl ester is obtained after filtration. The optical detection of a chiral chromatographic column is 99.2%, and the yield is 88.9%.

The fourth time for reusing the Catalyst A:

1. Dissolving 66 g (0.29 mol) of indanone ester in 132 g of toluene, and then putting the above recovered Catalyst A into the system. Dripping into the system 45.7 g (0.41 mol) of aqueous solution of tert-butyl hydroperoxide with mass fraction 80%. Dripping time is 3 h and the reaction temperature is 75-80° C.

2. After the oxidant is dripped, maintaining the temperature at 75-80° C. for 1 h. Taking the sample to inspect the reaction.

3. After tracking reaction and confirming the reaction is qualified, cooling down to 60~65° C., and Catalyst A is recovered by hot filtration.

4. Concentrating the filtrate and toluene which the weight is 70% of the weight of the added solvent is concentrated from the filtrate. Cooling it to 0~5° C., and maintaining the temperature for 1 h. 61.0 g of white solid (2S)-5-chloro-2,3-dihydro-2-hydroxy-1-oxo-1H-indene-2-carboxylic acid methyl ester is obtained after filtration. The optical detection of a chiral chromatographic column is 99.5%, and the yield is 87.5%.

The fifth time for reusing the Catalyst A:

1. Dissolving 66 g (0.29 mol) of indanone ester in 132 g of toluene, and then putting the above recovered Catalyst A into the system. Dripping into the system 45.7 g (0.41 mol) of aqueous solution of tert-butyl hydroperoxide with mass fraction 80%. Dripping time is 3 h and the reaction temperature is 75-80° C.

2. After the oxidant is dripped, maintaining the temperature at 75-80° C. for 1 h. Taking the sample to inspect the reaction.

3. After tracking reaction and confirming the reaction is qualified, cooling down to 60~65° C., and Catalyst A is recovered by hot filtration.

4. Concentrating the filtrate and toluene which the weight is 70% of the weight of the added solvent is concentrated from the filtrate. Cooling it to 0~5° C., and maintaining the temperature for 1 h. 61.4 g of white solid (2S)-5-chloro-2,3-dihydro-2-hydroxy-1-oxo-1H-indene-2-carboxylic acid methyl ester is obtained after filtration. The optical detection of a chiral chromatographic column is 99.0%, and the yield is 88.1%.

Embodiment 3 (Taking Catalyst B as an Example)

1. Adding 28 g (0.1 mol) of 3-tert-butyl-5-styrylsalicylaldehyde and 5.7 g (0.05 mol) of (1S,2S)-(+)-1,2-cyclohexanediamine to a reaction flask, then adding 57 g of methanol to the reaction flask and the mixture is heated and refluxed. Cooling the mixture to 0~5° C. and a yellow condensate solid is obtained after filtration. The weight of the condensate solid is weighed as 28.75 g after drying, and the yield is 90%.

2. Weighing and dissolving 12.78 g (0.02 mol) of the above dried condensate in 90 g of tetrahydrofuran, raising the temperature to 50~60° C., add 2.26 g (0.06 mol) of sodium borohydride in batches. After the reaction, removing the tetrahydrofuran. Adding 40 g of water into the system, extracting with 100 g of ethyl acetate. After removing ethyl acetate, adding 50 g of methanol to crystallize. Lowering the temperature to 0° C. and filtering to obtain 11.2 g of ligand monomer of Catalyst B, with a yield of 87%.

3. Adding 5.14 g (8 mmol) of Catalyst B ligand monomer into a pressure resistant reaction flask. Adding 50 g of ethanol/water and 0.05 g of AIBN. Hydrothermal polymerization is carried out at 115-120° C. for 24 h to obtain a white-like spherical polymer ligand. The polymerization degree is 800-1300, the particle size is 0.3-0.5 mm, and the dry weight is 5.2 g.

4. Adding 2.6 g (4 mmol) of the polymer ligand and 1.68 g (4 mmol) of n-propyl zirconate to 20 g of toluene. After complexation reaction at 75~80° C. for 24 h, a catalyst B toluene suspension system was obtained. The yield of the Catalyst A is calculated as 100% and its weight is 2.92 g.

5. Dissolving 66 g (0.29 mol) of indanone ester in 132 g of toluene, and then putting the mixture into the abovementioned 2.92 g (4 mmol) of Catalyst B toluene suspension system. Dripping into the system 45.7 g (0.41 mol) of aqueous solution of tert-butyl hydroperoxide with mass fraction 80%. Dripping time is 2.5 h and the reaction temperature is 75-80° C.

6. After the oxidant is dripped, maintaining the temperature at 75-80° C. for 1 h. Taking the sample to inspect the reaction.

7. After tracking reaction and confirming the reaction is qualified, cooling down to 60~65° C., and Catalyst B is recovered by hot filtration.

8. Concentrating the filtrate and toluene which the weight is 70% of the weight of the added solvent is concentrated from the filtrate. Cooling it to 0~5° C., and maintaining the temperature for 1 h. 60.68 g of white solid (2S)-5-chloro-2,3-dihydro-2-hydroxy-1-oxo-1H-indene-2-carboxylic acid methyl ester is obtained after filtration. The optical detection of a chiral chromatographic column is 99.3%, and the yield is 87.0%.

Embodiment 4 (Taking Catalyst B as an Example)

1. The polymer ligand is prepared first, which is the same as in Embodiment 3.

2. Adding 2.6 g (4 mmol) of the polymer ligand and 2.81 g (4 mmol) of zirconium trifluoroacetylacetonate to 20 g of toluene. After complexation reaction at 75~80° C. for 20 h, a catalyst B toluene suspension system was obtained. The yield of the Catalyst A is calculated as 100%.

3. Dissolving 66 g (0.29 mol) of indanone ester in 132 g of toluene, and then putting the mixture into the abovementioned Catalyst B toluene suspension system. Dripping into the system 45.7 g (0.41 mol) of aqueous solution of tert-butyl hydroperoxide with mass fraction 80%. Dripping time is 2.5 h and the reaction temperature is 75-80° C.

4. After the oxidant is dripped, maintaining the temperature at 75-80° C. for 1 h. Taking the sample to inspect the reaction.

5. After tracking reaction and confirming the reaction is qualified, cooling down to 60~65° C., and Catalyst B is recovered by hot filtration.

6. Concentrating the filtrate and toluene which the weight is 70% of the weight of the added solvent is concentrated from the filtrate. Cooling it to 0~5° C., and maintaining the temperature for 1 h. 60.2 g of white solid (2S)-5-chloro-2, 3-dihydro-2-hydroxy-1-oxo-1H-indene-2-carboxylic acid methyl ester is obtained after filtration. The optical detection of a chiral chromatographic column is 99.1%, and the yield is 86.3%.

The invention adopts a new catalyst in the preparation of indoxacarb, which is a polymer compound with high catalytic efficiency and is easy to recycle and utilize. For the production of indoxacarb with the same quality, the catalyst consumption is only one-third of that of DuPont Company, and the catalyst can be recycled and utilized for more than 5 times without adding new catalyst. The content of the hydroxyl intermediate S-enantiomer of the indoxacarb is kept above 99%. The cost per ton of high optical indoxacarb is reduced more than RMB 50000 yuan compared with that of DuPont Company, which greatly improves the market competitiveness of the products.

The invention claimed is:

1. A preparation method for a high optical indoxacarb intermediate (2S)-5-chloro-2,3-dihydro-2-hydroxy-1-oxo-1H-indene-2-carboxylic acid methyl ester, wherein an asymmetric synthesis is catalyzed by a chiral Zr-salen polymer, a method of producing the chiral Zr-salen polymer, comprising the steps of:

(1) adding a solvent I, 3-tert-butyl-5-styrylsalicylaldehyde and (1S,2S)-(−)-1,2-diphenylethylenediamine or (1S,2S)-(+)-1,2-cyclohexanediamine into a reaction flask, raising the temperature for reflux reaction, after the reaction is finished, a condensate is obtained after lowering the temperature and filtration, wherein the solvent I is methanol;

(2) dissolving the condensate in a solvent II, raising the temperature to 50-60° C., and dripping a reducing agent, removing the solvent II after the reaction, adding water into the system, and a ligand monomer of catalyst A or catalyst B is obtained after extraction, desolvation, crystallization, lowering the temperature and filtration, wherein the solvent II is tetrahydrofuran;

(3) putting the ligand monomer of catalyst A or catalyst B into a pressure-resistant reaction flask, adding a solvent III and using azobisisobutyronitrile (AIBN) as an initiator, carrying out hydrothermal polymerization at 110-120° C., then a polymer ligand is obtained after filtration and drying, wherein the solvent III is a mixture of ethanol and water;

(4) putting the polymer ligand and a zirconium-containing metal compound in toluene at 50-80° C. to carry out complexation reaction, after the reaction, a toluene system of catalyst A or catalyst B is obtained, wherein the zirconium-containing metal compound is selected from zirconium hydroxide, zirconyl chloride octahydrate, zirconium dioxide, zirconium(IV) acetylacetonate, zirconium trifluoroacetylacetonate, n-propyl zirconate, zirconium(IV) tert-butoxide, zirconium (IV) hydrogenphosphate, zirconium(IV) bromide, and mixtures thereof;

and the preparation reaction equation is as follows:

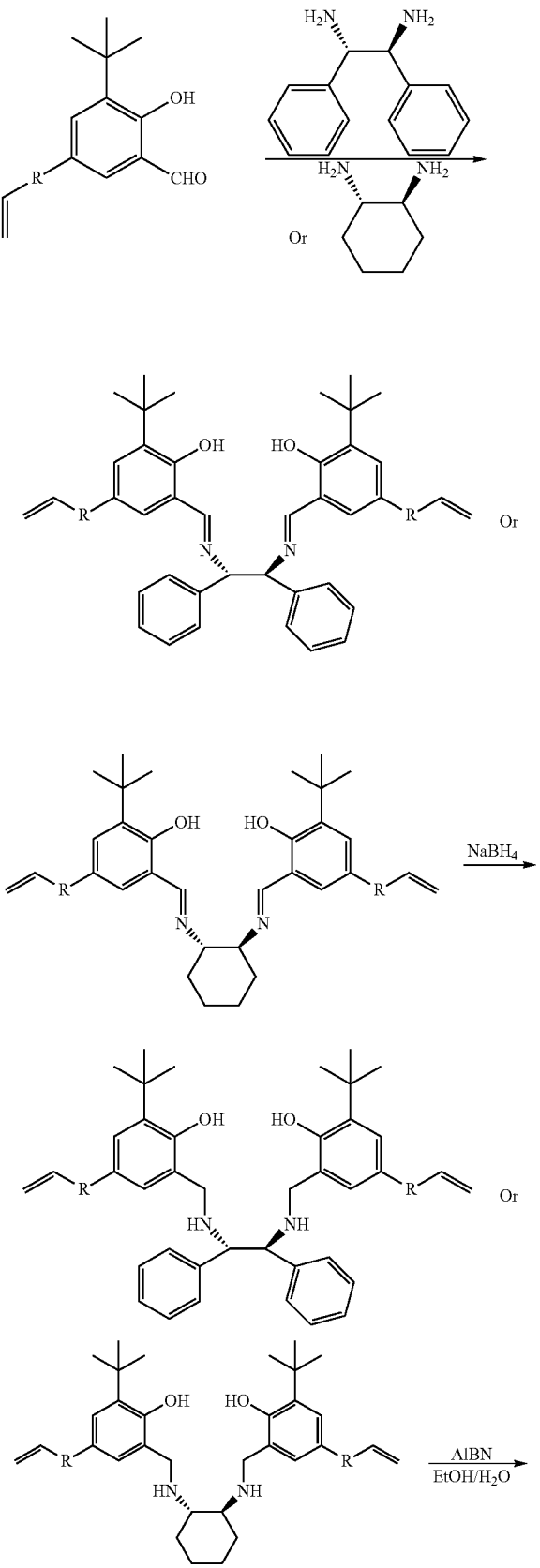

13
-continued
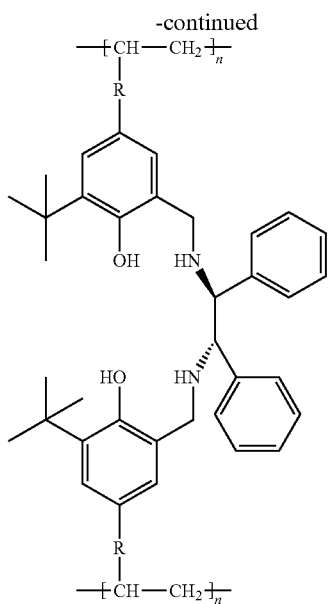
Or
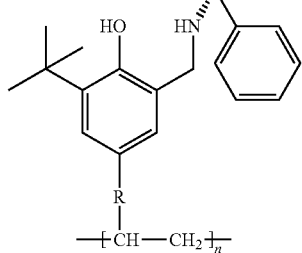
Zr—X→
14
-continued
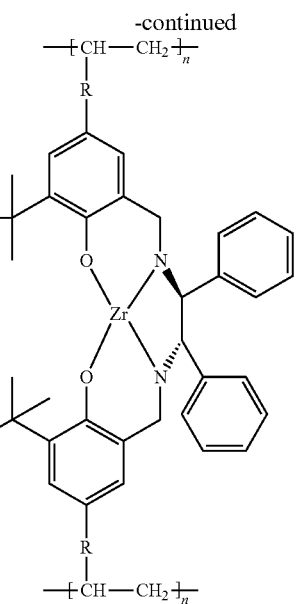
Or
Catalyst A
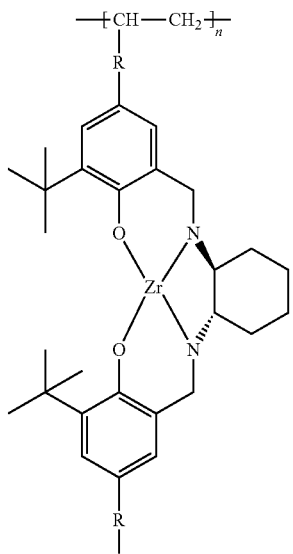
Catalyst B
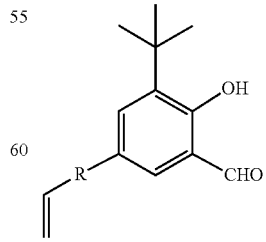
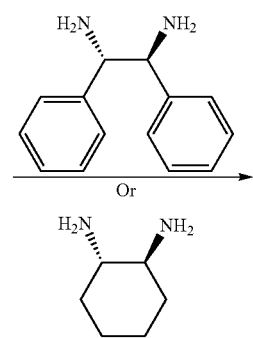
Or

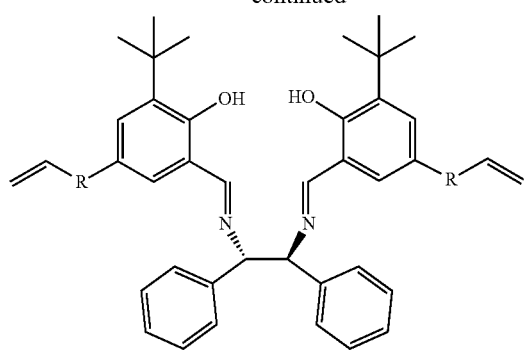
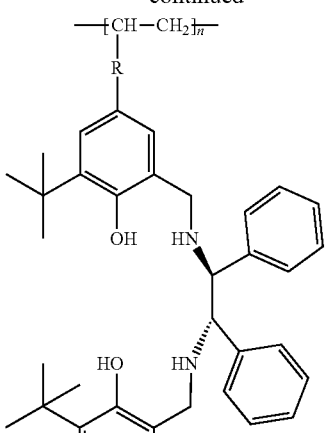
Or
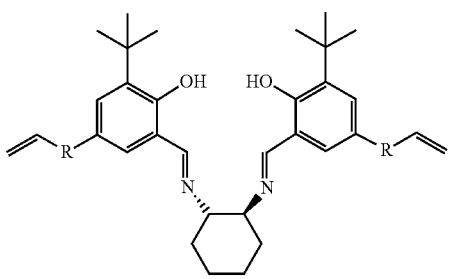
Reducing agent →
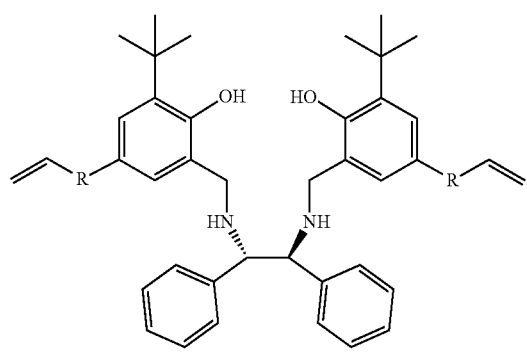
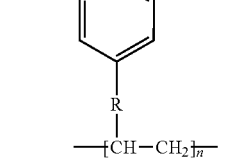
Or
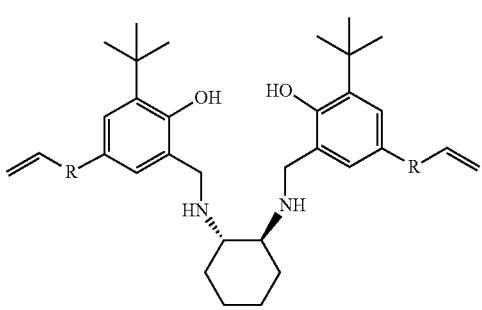
AIBN
EtOH/H₂O →
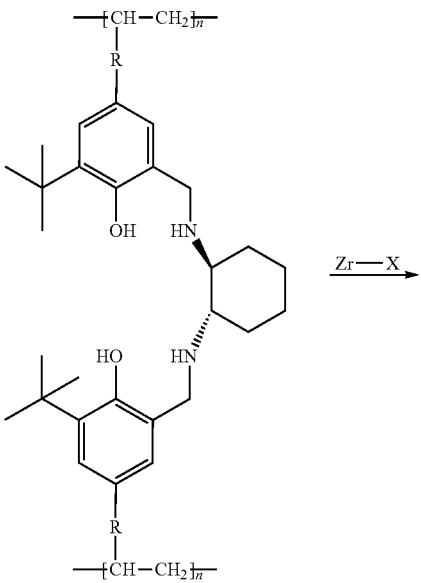
Zr—X →

17

-continued

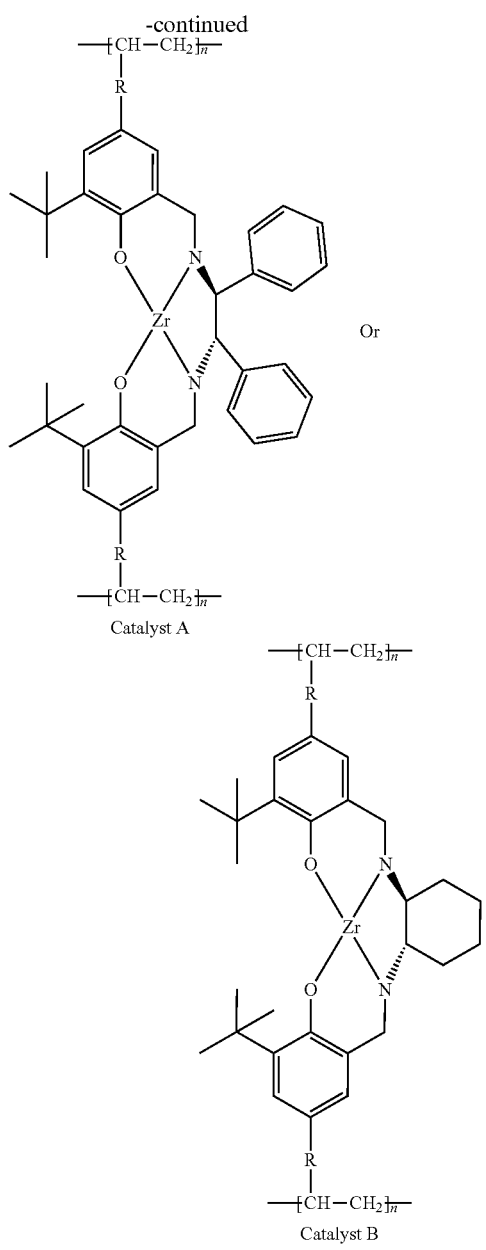

Catalyst A

Catalyst B wherein: R is

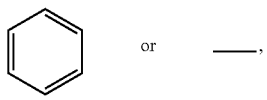 or —, n is 100~20000, and Zr—X is the zirconium-containing metal compound.

2. The preparation method for the high optical indoxacarb intermediate according to claim 1, comprising the steps of: adding 5-chloro-2-methoxycarbonyl-1-indanone ester in toluene solution into the toluene system of catalyst A or catalyst B obtained by the above method, dripping an oxidant at 50-80° C. to carry out asymmetric synthesis reaction, after the reaction is finished, cooling it to 60-65° C.; Catalyst A or Catalyst B is recovered by hot filtration, after the filtrate is concentrated, cooled and filtered, the high optical indoxacarb intermediate (2S)-5-chloro-2,3-dihydro-2-hydroxy-1-oxo-1H-indene-2-carboxylic acid methyl ester is obtained; at the same time, the recovered Catalyst A or Catalyst B is put into toluene solvent to form a suspension, which can continue to participate in the above asymmetric synthesis reaction.

3. The preparation method for the high optical indoxacarb intermediate (2S)-5-chloro-2,3-dihydro-2-hydroxy-1-oxo-1H-indene-2-carboxylic acid methyl ester according to claim 1, wherein in step (1), a duration of the reflux reaction is 6-7 h; a mole ratio of 3-tert-butyl-5-styrylsalicylaldehyde and (1S,2S)-(−)-1,2-diphenylethylenediamine or (1S,2S)-(+)-1,2-cyclohexanediamine is 2:1-1.1; a dosage of the solvent I is 8-10 times of the mass of (1S,2S)-(−)-1,2-diphenylethylenediamine or (1S,2S)-(+)-1,2-cyclohexanediamine.

4. The preparation method for the high optical indoxacarb intermediate (2S)-5-chloro-2,3-dihydro-2-hydroxy-1-oxo-1H-indene-2-carboxylic acid methyl ester according to claim 1, wherein in step (2), the reducing agent is sodium borohydride or sodium cyanoborohydride or potassium borohydride or lithium aluminum hydride; a mole ratio of the reducing agent and the condensate is 2-4:1; a dosage of the solvent II is 4-8 times of the mass of the condensate.

5. The preparation method for the high optical indoxacarb intermediate (2S)-5-chloro-2,3-dihydro-2-hydroxy-1-oxo-1H-indene-2-carboxylic acid methyl ester according to claim 1, wherein a weight of the water added in step (2) is 2-4 times of the weight of the condensate; extraction with ethyl acetate, and a weight of ethyl acetate added is 6-10 times of the weight of the condensate; the crystallization solvent is methanol; a dosage of methanol is 4-8 times of the weight of the condensate.

6. The preparation method for the high optical indoxacarb intermediate (2S)-5-chloro-2,3-dihydro-2-hydroxy-1-oxo-1H-indene-2-carboxylic acid methyl ester according to claim 1, wherein in step (3), a volume ratio of ethanol to water in the solvent III is 3:1; a dosage of the solvent III is 6-10 times of the weight of the ligand monomer of Catalyst A or Catalyst B, and a dosage of AIBN is 0.5%~2% of the weight of the ligand monomer of Catalyst A or Catalyst B.

7. The preparation method for the high optical indoxacarb intermediate (2S)-5-chloro-2,3-dihydro-2-hydroxy-1-oxo-1H-indene-2-carboxylic acid methyl ester according to claim 1, wherein in step (3), a particle size of the polymer ligand is 0.1-1 mm.

8. The preparation method for the high optical indoxacarb intermediate (2S)-5-chloro-2,3-dihydro-2-hydroxy-1-oxo-1H-indene-2-carboxylic acid methyl ester according to claim 1, wherein in step (4), a mole ratio of the polymer ligand to the zirconium-containing metal compound is 1-1.5:1; a dosage of the toluene is 4-10 times of the weight of the polymer ligand.

9. The preparation method for the high optical indoxacarb intermediate (2S)-5-chloro-2,3-dihydro-2-hydroxy-1-oxo-1H-indene-2-carboxylic acid methyl ester according to claim 2, wherein the oxidant is tert-butyl hydroperoxide or m-chloroperbenzoic acid or cumyl hydroperoxide; in terms of the mole ratio of pure matter, the oxidant to 5-chloro-2-methoxycarbonyl-1-indanone ester is 1:1.2-3; an added dosage of catalyst A or catalyst B is 1%-5% of the mass of 5-chloro-2-methoxycarbonyl-1-indanone ester; in the 5-chloro-2-methoxycarbonyl-1-indanone ester in toluene solution, a dosage of toluene is 2-4 times of the weight of 5-chloro-2-methoxycarbonyl-1-indanone ester.

10. The preparation method for the high optical indoxacarb intermediate (2S)-5-chloro-2,3-dihydro-2-hydroxy-1-oxo-1H-indene-2-carboxylic acid methyl ester according to claim 1, wherein the reducing agent in the preparation reaction equation is sodium borohydride.

\* \* \* \* \*